(12) United States Patent
McNamara

(10) Patent No.: US 7,837,984 B2
(45) Date of Patent: Nov. 23, 2010

(54) POST-FOAMING COSMETIC COMPOSITION AND METHOD EMPLOYING SAME

(75) Inventor: William E. McNamara, Chester, NY (US)

(73) Assignee: Avon Products, Inc., New York, NY (US)

( * ) Notice: Subject to any disclaimer, the term of this patent is extended or adjusted under 35 U.S.C. 154(b) by 569 days.

(21) Appl. No.: 10/331,069

(22) Filed: Dec. 27, 2002

(65) Prior Publication Data

US 2004/0126345 A1 Jul. 1, 2004

(51) Int. Cl.
*A61Q 1/10* (2006.01)
*A61Q 5/00* (2006.01)

(52) U.S. Cl. ............... 424/70.7; 424/401; 424/70.1

(58) Field of Classification Search ............... None
See application file for complete search history.

(56) References Cited

U.S. PATENT DOCUMENTS

| | | | |
|---|---|---|---|
| 3,541,581 A | 11/1970 | Monson | |
| 3,876,771 A | 4/1975 | Denner | |
| 4,528,111 A | 7/1985 | Su | |
| 5,389,363 A | 2/1995 | Snyder et al. | |
| 5,800,825 A | 9/1998 | McMullen | |
| 5,853,712 A * | 12/1998 | Langlois | 424/78.03 |
| 6,027,738 A | 2/2000 | Stepniewski et al. | |
| 6,030,630 A | 2/2000 | Fleury et al. | |
| 6,096,702 A | 8/2000 | Ramirez et al. | |
| 6,177,092 B1 | 1/2001 | Lentini et al. | |
| 6,214,329 B1 * | 4/2001 | Brieva et al. | 424/70.7 |
| 6,224,851 B1 | 5/2001 | Bara | |
| 6,251,375 B1 | 6/2001 | Bara | |
| 6,274,131 B1 * | 8/2001 | Piot et al. | 424/70.7 |
| 6,328,950 B1 | 12/2001 | Franzke et al. | |
| 6,440,923 B1 | 8/2002 | Lyle et al. | |
| 2002/0122772 A1 * | 9/2002 | Lukenbach et al. | 424/44 |

FOREIGN PATENT DOCUMENTS

| | | |
|---|---|---|
| EP | 1216684 A1 | 6/2002 |
| JP | 03-31389 A | 2/1991 |
| JP | 03-178923 A | 8/1991 |
| JP | 07-53325 A | 2/1995 |
| JP | 08-73839 A | 3/1996 |
| JP | 52-5683 A | 1/1997 |
| JP | 09-77629 A | 3/1997 |
| WO | 2003/043598 A1 | 5/2003 |

OTHER PUBLICATIONS

U.S. Appl. No. 10/502,061, filed Apr. 8, 2005, W. McNamara et al.
U.S. Appl. No. 10/532,361, filed Apr. 20, 2005, W. McNamara et al.
U.S. Appl. No. 10/532,362, filed Apr. 20, 2005, W. McNamara et al.

* cited by examiner

*Primary Examiner*—Jyothsna A Venkat
(74) *Attorney, Agent, or Firm*—Charles J. Zeller; Joan M. McGillycuddy; Anthony M. Santini

(57) ABSTRACT

The present invention provides a composition for application to keratin fibers, preferably hair, more preferably the hair of the scalp, eyebrows and eyelashes, and most preferably the eyelashes. The composition comprises a post-foaming gel containing a film forming agent and, optionally, a colorant, preferably a pigment. The present invention also provides a method for imparting a volumizing effect to hair of the scalp, eyebrows or eyelashes.

22 Claims, No Drawings

POST-FOAMING COSMETIC COMPOSITION AND METHOD EMPLOYING SAME

BACKGROUND OF THE INVENTION

1. Field of the Invention

The present invention provides a composition for application to keratin fibers, preferably hair, more preferably the hair of the scalp, eyebrows and eyelashes, and most preferably the eyelashes. The composition comprises a post-foaming gel composition containing a film forming agent and, optionally, a colorant, preferably a pigment. The present invention also provides a method for imparting a volumizing effect to hair of the scalp, eyebrows or eyelashes.

2. Description of the Related Art

Prior to the present invention, personal care preparations for the volumizing of hair, in particular eye lashes, employed the use of mascara in a building fashion. That is several coats had to be applied to gain the desired volume or expansion effect. Depending on the type of mascara product and consumer preferences the amount of manipulation required could be quite extensive. This is evident in the large number of brush strokes needed to arrive at a clump-free yet volumized look. Currently, it has been observed that women use an average approximately 10 to 12 brush strokes to apply mascara to one pair of eyelashes. Depending upon the user, this number of brush strokes can be multiplied by 2 to 4 times depending on the desired level of volume. Women desire a mascara composition that can achieve the appearance of thicker eyelashes with a lower number of brush strokes, i.e., less manipulation, or even improved thickness with the same amount of brush strokes. Consumers, men and women alike, also desire products that will provide the appearance of thicker hair.

Post-foaming gels are known in the art, for example U.S. Pat. No. 3,541,581 discloses a cleansing or cosmetic composition in the form of a stable, post-foaming gel. The disclosed gel has a yield value sufficiently high to substantially restrain the composition from foaming for at least about 60 seconds under static ambient conditions. The '581 patentee states that an object of the invention is to provide a lather-producing composition that, in addition to possessing the desirable properties of prior art compositions, is characterized by being discharged as a stable gel that is substantially free from foaming. After it is spread over the skin and beard, the gel produces a post generating foam. The purpose of the invention is to provide a lather, in-situ, on the surface of the skin so as to facilitate shaving of facial hair. The invention is also disclosed to be useful in topical applications for cleansing. Moreover, coloring materials, such as dyes may be used if desired.

U.S. Pat. No. 4,405,489 discloses a process for continuously producing a post-foaming gel and for packaging same. The process comprises admixing separately metered amounts of an aqueous soap ingredient and a post-foaming agent to form an intimate mixture thereof. The mixture is passed to a filling machine for packaging the gel. The steps are affected in a continuous flow system under pressure. The mixture is maintained within the continuous flow system for a time and at a pressure and temperature sufficient to produce a post-foaming gel that is capable of continuously flowing through the system to the filling machine for packaging thereof.

U.S. Pat. No. 4,651,503 is also directed to a method for forming and packaging a delayed foaming gel. The disclosed invention forms an emulsion in the filling head and then forms the delayed foaming gel in the container after it is filled therein.

U.S. Pat. No. 4,528,111 discloses a stable shaving cream gel that is asserted to possess superior foaming and after-feel characteristics. Various compatible additives which do not adversely affect the gel structure may be added in minor amounts. Included among the materials exemplified as suitable for such purpose are coloring materials. A combination of the dyes D & C Yellow #10 and F D & C Blue #1 is employed in Examples 6 through 10. They are however used in very low concentration. For example 1.2% of a 1% trituration of D & C Yellow #10 dye and 0.45% of 1% trituration F D & C Blue #1 dye are employed in Example 7.

Though the post-foaming compositions of the prior have been used for shaving facial hair and though such compositions may contain minor amounts of a dye to impart to the composition a coloration more pleasing to the consumer, such compositions have heretofore found no further use. The present inventor has discovered that the delayed post-foaming compositions of the prior art can be surprisingly and advantageously modified and employed to improve the aesthetic appearance of keratin fibers, especially hair of the scalp, eyebrows or eyelashes.

SUMMARY OF THE INVENTION

The present invention relates to a composition for application to keratin fibers such as hair fibers of the scalp, eyebrows and eyelashes. More particularly, the invention relates to a post-foaming composition for such purpose and to a method of using such composition to impart volume and/or color to keratin fibers of the scalp, eyebrows and eyelashes.

The present invention, in brief summary, is a composition including a gel having a film-forming agent present in an amount effective to form a film after the composition is applied to a keratin fiber or a colorant present in an amount sufficient to mask color of the foam formed after the composition is applied to a keratin fiber, and preferably both.

DETAILED DESCRIPTION OF THE INVENTION

The composition of the present invention is comprised of a post-foaming gel and a film forming agent or a colorant, and preferably both.

The post-foaming gel of the present invention may be further incorporated into a cosmetic composition. However, to best achieve the desired benefits of the present invention, it is preferred that the composition includes at least 85% by weight, and more preferably at least 95% by weight, of the gel based upon the total weight of the composition. Most preferably, the composition is 100% by weight of the post-foaming gel.

Post-Foaming Gel Component

Post-foaming gels are known in the art. For purposes of the present invention, a post-foaming gel is a gel that does not create a foam as it is dispensed from its container, but creates a foam after exposure to atmospheric pressure for at least 2 seconds. However, a post-foaming gel may foam even sooner when exposed to mechanical manipulation and/or to temperatures greater than ambient temperature. Such post-foaming gels are also within the scope of the present invention.

It should be appreciated that any post-foaming gel component can be employed in preparing the compositions of the present invention. The post-foaming gel of U.S. Pat. Nos. 2,995,521; 3,541,581; 3,654,167; 4,405,489; 4,528,111; 4,651,503; 6,165,456 and U.S. Patent Application Publication US 2002/0122772 A1, the entire disclosures of which are incorporated herein by reference, are non-limiting examples of suitable post-forming gels. The post-foaming gel of U.S. Pat. Nos. 3,541,581; 4,528,111 and U.S. Patent Application Publication US 202/0122772 A1 are preferred. The post-foaming gel of U.S. Pat. No. 3,541,581 is most preferred in the present invention. For ease of removal of the composition, using a water-rinseable post-foaming gel component is preferred.

When the composition of the present invention utilizes a post-foaming gel component as described in U.S. Pat. No. 3,541,581, the composition is in the form of a stable, post-foaming gel comprised of about 30 to about 90% by weight water; a surfactant selected from a group consisting of anionic, nonionic, amphoteric surfactants and mixtures thereof, with the proviso that when a water-soluble salt of a fatty acid is employed as surfactant, it is present in an amount of about 0.1 to about 20% by weight and when the surfactant employed is other than a water-soluble salt of a fatty acid, it is present in an amount of about 0.1 to about 12.0% by weight; about 0.1 to about 15% by weight of volatile liquid post-foaming material selected from the group consisting of aliphatic hydrocarbons, halogenated hydrocarbons and mixtures thereof, about 0.1 to about 0.8% by weight of an antimicrobial or preservative; about 1 to about 30% by weight of a polymer film forming agent (preferably acrylates copolymer); about 0.5 to about 15% by weight of pigment (including coated and uncoated pigments and combinations thereof); and about 0.01 to about 5% by weight of at least one water-soluble gelling agent which when incorporated in the composition provides a gel having a sufficiently high yield value as to restrain the composition from foaming for at least 2, preferably 5, and more preferably 10 seconds, under static ambient conditions and/or in combination with mechanical manipulation, e.g., with a mascara applicator. A composition of the present invention utilizing the post-foaming gel in accordance with U.S. Pat. No. 3,541,581 is further described in Example 1 of the present application.

Although the focus has been on the use of a post-foaming gel component in accordance with U.S. Pat. No. 3,541,581, as noted earlier, any topically acceptable post-foaming gel can be employed as the post-foaming gel of the present invention. For example the post-foaming gel composition of U.S. Pat. No. 4,528,111 or the self-foaming gel of US patent application publication US 2002/0122772 A1.

The post-foaming gel component of U.S. Pat. No. 4,528,111 is provided by the interpolymer gel reaction products of selective anionic polymers, and selective cationic polymers. This gel is a water soluble interpolymer gel reaction product formed by the rapid and intensive interaction of two oppositely charged selective polymers; a quatemized cationic polymer bearing positive charges and selected from the group consisting of poly(diallyldimethylchloride-co-acrylamide) and a quaternary ammonium cellulose ether polymer, and an anionic polymer bearing negative charges and selected from the group consisting of poly(2-acrylamido-2-methylpropane sulfonic acid) and alginic acid. The selective group of anionic polymers include: Polysulfonic acid ("PSA") such as poly(2-acrylamido-2-methylpropane sulfonic acid) available as POLYMER HSP 1180 from Henkel as a 15% aqueous solution and alginic acid in free acid form, which is water insoluble and available as a powder. Particularly, what is needed is about 0.05-5%, preferably 0.1-1.0%, of a water soluble interpolymer gel reaction product of a quatemized cationic polymer selected from the group consisting of poly(diallyldimethyl chloride-co-acrylamide) and a quaternary ammonium cellulose ether polymer, and an anionic polymer selected from the group consisting of poly(2-acrylamido-2-methylpropane sulfonic acid) and alginic acid; and about 55-94% water.

The method of preparing interpolymer gels that can be employed for purposes of the present invention comprises the rapid mixing, at a rate of at least 1000 rpm, of high concentrations of the aforesaid selective anionic and selective cationic polymers in an aqueous medium substantially free of interfering ingredients, such as salt, amphoteric, anionic and cationic compounds. The selective group of quatemized cationic polymers used in the preparation of the water soluble interpolymer gels are water soluble and include: poly(diallyldimethylammonium chloride-co-acrylamide), which is the copolymer of dimethyldiallylammonium chloride and of acrylamide, having a molecular weight of more than 500,000, and sold under the name MERQUAT 550 and MERQUAT S by the Merck Company and obtainable as an 8% aqueous solution.

The interpolymer reactions of polycationic and polyanionic materials produce reaction products ranging from insoluble precipitates to water soluble and water insoluble but swellable gels. The reaction product of poly(2-acrylamido-2-methylpropane sulfonic acid) (PSA) and MERQUAT 550 loses its fluidity and forms a clear gel at 7.5% PSA and 4% MERQUAT 550, while the individual solutions flow freely. The minimum concentration required for the formation of the interpolymer gel reaction product of PSA and MERQUAT 550 is 7.5% PSA and 4% MERQUAT 550. The aqueous reaction mixture, which is the sum total of both solutions, contains 3.75% PSA and 2% MERQUAT 550. The gel, when diluted to 1.89% PSA and 0.96% MERQUAT 550, still exhibits a high viscosity of more than 24,000 cps, while the individual solutions show a viscosity of 400 cps and 200 cps, respectively. This gel is prepared by vigorously mixing a 7.5-15% solution of PSA and 4-8% solution of MERQUAT 550. Slow mixing results in white precipitates within the gel. Further dilution of the two solutions before mixing also results in white precipitates when they are mixed. This clearly indicates that it requires fast and intensive interactions of the two opposite charges to ensure maximum amount of ion pair formation to give the gel structure. Whether the gel is water-soluble or water-insoluble depends on the formation of intimate or loose ion pairs which, in turn, depends on the charge density and structure of the polyelectrolytes.

As noted earlier herein, the post-foaming gel of US Patent Application Publication US 2002/0122772 A1 can be employed as the post-foaming gel component for the present invention. By combining an anionic surfactant, an amphoteric surfactant and, possibly, a nonionic surfactant, with a self-foaming agent one can create an effective post-foaming gel. The first component of the system is one or more anionic surfactants. Preferably, the anionic surfactant is selected from alkyl sulfates; alkyl ether sulfates; alkyl monoglyceryl ether sulfates; alkyl monoglyceride sulfates; alkyl monoglyceride sulfonates; alkyl sulfonates; alkylaryl sulfonates; alkyl sulfosuccinates; alkyl ether sulfosuccinates; alkyl sulfosuccinates; alkyl amidosulfosuccinates; alkyl carboxylates; alkyl amidoethercarboxylates; alkyl succinates; fatty acyl sarcosinates; fatty acyl amino acids; fatty acyl taurates; fatty alkyl sulfoacetates; alkyl phosphates; alkyl ether phosphates; and mixtures thereof. A preferred anionic surfactant is sodium laureth sulfate.

The second component of a post-foaming gel component according to 2002/0122772 A1 is an amphoteric surfactant. Examples of amphoteric surfactants that can be employed include amphocarboxylates, alkyl betaines, amidoalkyl betaines, amidoalkyl sultaines, amphophosphates, phosphobetaines, pyrophosphobetaines, carboxyalkyl alkyl polyamines, alkyl amino monoacetates, alkyl amino diacetates, and mixtures thereof. Betaine amphoteric surfactants are preferred. Cocamidopropyl betaine is most preferred.

An optional component of the post-foaming gel component is one or more nonionic surfactants. One class of nonionic surfactants useful in the present invention are polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, alpha-methyl glucoside, polyglucose having an average of about 1 to about 3 glucose residues per molecule, glycerin, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester.

Examples of preferred polyoxyethylene derivatives of polyol esters include PEG-80 sorbitan laurate and Polysorbate 20. PEG-80 sorbitan laurate, which is a sorbitan monoester of lauric acid ethoxylated with an average of about 80 moles of ethylene oxide, is available commercially from ICI Surfactants of Wilmington, Del. under the tradename, "ATLAS G-4280." Polysorbate 20, which is the laurate monoester of a mixture of sorbitol and sorbitol anhydrides condensed with approximately 20 moles of ethylene oxide, is available commercially from Uniqema Company under the trade name "TWEEN 20."

Another class of suitable nonionic surfactants includes long chain alkyl glucosides or polyglucosides, which are the condensation products of (a) a long chain alcohol containing from about 6 to about 22 carbon atoms, preferably from about 8 to about 14 carbon atoms, with (b) glucose or a glucose-containing polymer. The alkyl glucosides have about 1 to about 6 glucose residues per molecule of alkyl glucoside. Alkyl glucosides are the preferred nonionic surfactants. Suitable alkyl glucosides include, but are not limited to, octyl glucoside, decyl glucoside, and lauryl glucoside.

Additional nonionic surfactants that may be used include: ethylene oxide/propylene oxide copolymers, (poly)glycerol esters and fatty acids, fatty acid alkanolamides, alkoxylated mono and di-alkanolamides, aminoxides, ethoxylated fatty alcohols and esters, fatty acid sucrose esters, ethoxylated glucosides, and fatty gluconamides.

Film Forming Agent

The film forming agent is present in an amount sufficient so that when the composition is applied to the hair of the scalp, eyebrows or eyelashes, and the post-foaming gel begins to foam, the film formed by the film forming agent will stabilize at least a portion of the foam (as will be elaborated on more fully below) thereby imparting a volumizing effect to the hair fibers upon which the composition is applied.

The film forming agent can be natural or synthetic. Film forming waxes are known in the art and can be employed alone or in combination with one or more natural or synthetic film forming agents. Synthetic film forming agents are particularly preferred. Film forming agents that can be utilized include, acrylates copolymers and/or methacrylates copolymers. Suitable, non-limiting examples of film-forming agents useful in the present invention include sodium acrylates copolymer, sodium acryloldimethyl taurate copolymer, ethyl methacrylate/N-butyl acrylate/2-methylhexyl acrylate copolymer, and butyl acrylate/hydroxyethyl methacrylate copolymer. Polymeric blends, such as Interpolymer's SYN-TRAN EX-100 and Kobo Product's DAITOSOL 5000 SJ are also useful as synthetic polymer film forming agent in the composition of the present invention. Preferably, the film forming agent is employed in a concentration of from about 1 to about 50% by weight, more preferably about 5 to about 40% by weight, most preferably about 10 to about 30% by weight, and optimally about 15 to about 25% by weight, based on the total weight of the gel. As will be discussed below, the post-foaming gel may contain a pigment dispersion that includes one or more film forming agents, the amount of film forming agent contributed by the pigment dispersion is considered in the total amount of film forming agent in the post-foaming gel. For example, if the post-foaming gel contains 50 wt %, based on the total weight of the post-foaming gel, of a pigment dispersion that further contains 40 wt %, based on the total weight of the pigment dispersion, of a film forming agent, the post-foaming gel has 20 wt % film forming agent (due to the contribution of the pigment dispersion). Additional film forming agent may be added to a total of about 50 wt % based upon the total weight of the post-foaming gel.

While the inventor does not wish to be bound to any one theory it is believed that during the post-foaming action the film forming agent will set, thus, locking or sealing the foam lattice in place, either by forming a film, preferably a flexible film, over at least a portion of the surface of the foam or by increasing the rigidity of the foam lattice thereby stabilizing the foam. Preferably, a film will form over greater than about 50 percent of the surface of the foam, and more preferably over greater than about 75 percent of the surface of the foam. Alternatively, the film forming agent increases the rigidity of the foam lattice by greater than about 50%, and more preferably by greater than about 75%.

Since the compositions of the present invention are preferably used as cosmetic compositions for application to the hair, eyebrow and eyelashes, it is preferred that the film forming agent is of the type and amount to allow the composition to be removed from the user with water, mild soap or a mild cosmetic cleanser.

Colorant

The novel cosmetic composition of the present invention can be transparent or colored, preferably when it is to be applied to the eyelashes it is colored. Prior art post-foaming gels have included colorants as an optional ingredient to give the composition a pleasing appearance. The present invention incorporates colorants in amount sufficient to mask the color of the foam, which is usually white, so that when the compositions of the present invention are applied to the hair, impart a color other than white. The presence of the pigment in an amount sufficient to mask the color of the foam allows the present invention to be used as cosmetic compositions, such as a mascara, a hair-volumizing dye or colorant or an eyebrow composition, among others. The post-foaming gel preferably includes about 0.5 to about 30% by weight, more preferably about 1 to 15% by weight, and most preferably about 2 to about 10% by weight, pigment based upon the total weight of the post-foaming gel.

Thus, the present invention preferably includes as a component a colorant, preferably a pigment, most preferably a pigment dispersion containing one or more film forming agents, which are preferably film forming polymers. The pigment dispersion is preferred because of the physical attributes associated with a finely dispersed, clump free, color solution providing added film forming capability. A material that is particularly preferred, since it performs extremely well, is the material WSJ24BAMP available from Kobo Products. This material is comprised of water 43 to 50%, by weight; ethylmethacrylate/N-butylacrylate/2-methylhexyl acrylate copolymer 25 to 30%, by weight; iron II, III oxide 22 to 26% by weight; sodium acryloldimethyl taurate copolymer 0.1 to 5%, by weight; and 2-amino-2-methyl-1-propanol 0.1 to 5%, by weight. Dry pigments (Iron II, III oxide) may also be utilized and, when combined with the proper water-soluble polymeric film forming agents and properly dispersed, can accomplish the desired effect. The preferred material, WSJ24BAMP is generally employed in an amount of from about 5 to about 50% by weight, based on the total weight of the composition. It should be appreciated that in lieu of the about 0.5 to about 15% by weight of pigment, the composition can contain from about 0.5 to about 90% by weight of a pigment dispersion comprised of polymeric film forming agents, pigment, emulsifier and other adjuvants.

Optional Ingredients

Additional ingredients, such a vitamins, antioxidants, conditioning agents may also be incorporated into the present invention.

Cosmetic Composition

The present invention provides a self-foaming composition, which when applied foams or swells to a specified volume. One application merely requires perhaps 2 to 6 brush strokes in order to achieve the desired volume. Most desirably, the composition is applied to the eyelashes and the composition contains a sufficient amount of a pigment to mask the natural color of the foam so that the resultant composition can be employed as a mascara which due to its volumizing effect imparts a thickened appearance to the eyelashes upon which the composition is applied.

EXAMPLE 1

When the post-foaming cosmetic composition of the present invention employs a post-foaming gel as described in U.S. Pat. No. 3,541,581, the composition may include:

1. A solublizing component that provides lathering properties, is compatible with film forming agents and allows for the manufacture of a stable gel. Water, deionized, distilled or even tap water, is preferred as the solublizing component. It is generally employed in a range of about 30 to about 90% by weight, based on the total weight of the gel. It should be appreciated that when the composition is to be employed on the hair of the scalp, the solubilizing component can be an alcohol or mixture of one or more alcohols and water.
2. A water-soluble soap component selected from sodium, potassium and triethanolamine salts of high molecular weight fatty acids. Palmitic acid, stearic acid, oleic acid, myristic acid, palm and coconut oil fatty acids are preferred. Additionally, betaines and sultaines can be employed, alone or in combination with the previously mentioned sodium, potassium or triethanolamine salts of fatty acids, so as to accomplish the foaming action, or simply for boosting foaming. Typically, the water-soluble soap component is present in a concentration of from about 0.5 to about 25% by weight, based on the total weight of the gel.
3. A water-soluble viscosity increasing or gelling component selected from synthetic sucrose derivatives (such as carbomer), cellulose gums and hydrophilic colloids (such as carrageenans). The water-soluble viscosity increasing or gelling agent is generally employed in a concentration of from about 0.1 to about 5% by weight, based on the total weight of the gel, depending upon the choice of thickener.
4. A film forming agent in a concentration of from about 1 to about 50% by weight, based on the total weight of the gel.
5. A volatile aliphatic hydrocarbon post-foaming component having a vapor pressure from about 6 to 30 p.s.i.g. at a temperature of about 90 to 100° F. Examples of suitable hydrocarbon post-foaming agents include n-pentane, isopentane, n-butane, isobutane, isobutene, trichlorotrifluorethane, 1,2-dichloro, 1,1,2,2-tetrafluoroethane, neopentane, and mixtures thereof.
6. A colorant is optionally included in an amount from about 1 to about 70% by weight, based on the total weight of the gel. The colorant is preferably a pigment, and most preferably a pigment dispersion.
7. A preservative is optionally included. NIPASTAT, GERMABEN II, LIQUAPAR OIL, AND LIQUAPAR PE are examples of preservative systems that can be utilized. They are generally employed in a concentration of effective to inhibit microbial growth. Preferably, about 0.1 to about 0.8% by weight, based on the total weight of the gel, of preservative is used.

The following additional examples are offered merely to further illustrate the present invention, they are not intended to be limiting in any respect. It should be appreciated that unless otherwise indicated all percentages utilized herein are percent by weight, based on the total weight of the gel.

A general formula for a particularly preferred mascara formulation in accordance with the present invention is set forth in the following Example 1.

EXAMPLE 2

| Mascara formulation | |
|---|---|
| Ingredient | wt. % |
| Distilled water | QS |
| Surfactant or mixtures of surfactants* | 0.1–20 |
| Volatile hydrocarbon or mixture of hydrocarbons | 0.1–15 |
| Gelling agent | 0.01–5 |
| WSJ24BAMP (pigment/film forming agent/water mix) | 5–50 |
| SYNTRAN EX-100 (acrylates copolymer/water/surfactant) | 1–30 |
| Antimicrobial | 0.1–0.8 |

*It should be noted that when the surfactant is a water-soluble salt of a fatty acid, it is preferably employed in a concentration of about 0.1 to 20% and when it is an anionic surfactant other than a water-soluble salt of a fatty acid, or a nonionic surfactant, or amphoteric surfactant or mixture thereof, it is preferably employed in a concentration of about 0.1 to 12%.

EXAMPLE 3

| Mascara formulation | |
|---|---|
| Ingredient | wt. % |
| Deionized water | QS |
| Palmitic acid | 5.0 |
| Triethanolamine | 3.0 |
| WSJ24BAMP (Kobo products) | 29.35 |
| SYNTRAN EX-100 (Interpolymer) | 18.0 |
| AGAR 150C (TIC Gums) | 0.25 |
| Polyglycerol diisostearate | 0.45 |
| Isoceteth-20 | 0.45 |
| Cocamidopropyl betaine | 0.1 |
| GERMABEN II | 0.2 |
| SALCARE AST (Ciba Specialty Chemical) | 0.2 |
| Isopentane | 2.4 |

EXAMPLE 4

| Mascara formulation | |
|---|---|
| Ingredient | wt. % |
| Deionized water | QS |
| Hydroxyethyl cellulose | 0.50 |
| Oleth-3 phosphate | 0.50 |
| Isoceteth-20 | 0.50 |
| Palmitic acid | 4.0 |
| Triethanolamine | 1.0 |
| SYNTRAN EX-100 | 10 |
| DAITOSOL 5000 SJ | 12 |
| Cocamidopropyl betaine | 0.50 |
| WSJ24BAMP | 25.0 |
| GERMABEN II | 0.50 |

EXAMPLE 5

| Mascara formulation | |
|---|---|
| Ingredient | wt. % |
| Deionized water | QS |
| Hydroxyethyl cellulose | 0.50 |
| Oleth-3 phosphate | 0.50 |
| Isoceteth-20 | 0.50 |
| Palmitic acid | 2.0 |
| Triethanolamine | 1.0 |
| SYNTRAN EX-100 | 11 |
| DAITOSOL 5000 SJ | 12 |
| Cocamidopropyl betaine | 0.50 |
| WSJ24BAMP | 25.0 |
| GERMABEN II | 0.50 |

EXAMPLE 6

| Mascara formulation | |
|---|---|
| Ingredient | wt. % |
| Deionized water | QS |
| Hydroxyethyl cellulose | 0.50 |
| Oleth-3 phosphate | 0.50 |
| Isoceteth-20 | 0.50 |
| Palmitic acid | 4.0 |
| Triethanolamine | 1.0 |
| SYNTRAN EX-100 | 18.0 |
| DAITOSOL 5000 SJ | 12.0 |
| Cocamidopropyl betaine | 0.50 |
| WSJ24BAMP | 25.0 |
| Isopentane | 1.50 |
| LIQUAPAR | 0.50 |

EXAMPLE 7

| Mascara formulation | |
|---|---|
| Ingredient | wt. % |
| Deionized water | QS |
| Hydroxyethyl cellulose | 1.0 |
| Sodium laureth ether sulfate | 0.7 |
| SYNTRAN EX-100 | 18.0 |
| DAITOSOL 5000 SJ | 10.0 |
| Cocamidopropyl betaine | 3.0 |
| WSJ24BAMP | 25.0 |
| Isopentane | 1.50 |
| LIQUAPAR | 0.50 |

EXAMPLE 8

| Mascara formulation | |
|---|---|
| Ingredient | wt. % |
| Deionized water | QS |
| Palmitic acid | 4.0 |
| Triethanolamine | 1.5 |
| PEG-150 Distearate | 1.7 |
| Isoceteth-20 | 1.0 |
| MERQUAT S POLYMER (8% solu.) | 0.1 |
| PSA polymer (15% solu.) | 0.1 |
| SYNTRAN EX-100 | 10.0 |
| DAITOSOL 5000 SJ | 5.0 |
| WSJ24BAMP | 25.0 |
| Butane/Pentane (25/75) | 2.0 |
| GERMABEN II | 0.5 |

For use as a volumizer for hair other than eyelashes a particularly preferred general formulation is set forth in the following Example 9

EXAMPLE 9

| Volumizing Product for Hair (other than eyelashes) | |
|---|---|
| Ingredient | wt. % |
| Deionized water | QS |
| Water-soluble soap, foam booster or combination thereof | 0.1–10 |
| Volatile hydrocarbon or mixture of hydrocarbons | 0.1–15 |
| Gelling agent | 0.01–5 |
| Polymeric film forming agent/Derivatives of acrylates copolymer | 0.5–30 |
| Preservative | 0.1–1 |
| Fragrance | 0.001–3 |
| Conditioner | 0.01–5 |

EXAMPLE 10

A composition according to the present invention may be made according to the following example.

| Phase | Ingredient | Wt % |
|---|---|---|
| A | Deionized Water (DM) | 37.5 |
| A | Hydroxyethylcellulose (HEC) | 0.5 |
| B | Triethanolamine (TEA) | 1 |
| B | Oleth-3-Phosphate | 0.5 |
| B | Isoceteth-20 | 0.5 |
| B | Palmitic Acid | 4 |
| C | SYNTAN EX-100 | 18 |
| C | DAITOSOL 5000SJ | 12 |
| C | Cocamidopropyl Betaine | 0.5 |
| D | WSJ24BAMP | 25 |
| D | LIQUAPAR | 0.5 |

Procedure:

Sprinkle HEC into water under medium/slow (400-600 RPM) tripleL blade mix. Allow HEC to fully disperse with no clumps Cover and heat phase A to 75° C.

Add phase B ingredients about 3-5 minutes apart thereby allowing each to fully mix/disperse before adding the next Mix the combined phases A and B at 75° C. for 10 minutes Add phase C ingredients one at a time to the mixture of phases A and B allowing the batch temperature to come back up to 75° C. before adding next.

Mix the combination of phases A, B and C at 75° C. for 15 minutes

Remove heat and switch to sweep blade at 50 RPM

At 45° C., add pigment dispersion (WSJ24BAMP) slowly under sweep. Use spatula to scrape sides of beaker and ensure thorough mix At 30° C., add preservative under sweep Continue the sweeping mixing until the mixture reaches room temperature

EXAMPLE 11

A composition according to the present invention may be made according to the following example.

| Phase | Ingredient | Wt % |
|---|---|---|
| A | Demineralized Water (DM) | 41.8 |
| A | Hydroxyethylcellulose (HEC) | 1 |
| B | Syntan EX-100 | 18 |
| B | DAITOSOL 5000SJ | 10 |
| B | Sodium Laureth Ether Sulfate | 0.7 |
| B | Cocamidopropyl Betaine | 3 |
| C | WSJ24BAMP | 5 |
| C | LIQUAPAR | 0.5 |

Procedure:

Sprinkle HEC into water under slow (200-400 RPM) tripleL blade mix. Allow HEC to fully disperse with no clumps Add phase B ingredients about 3-5 minutes apart thereby allowing each to fully mix/disperse before adding the next Increase mix speed to 600 RPM. Cover and heat phases A and B to 60° C.

Continue to mix the mixture of phases A and B at 60° C. for 10 minutes

Remove heat and switch to sweep blade at 50 RPM

At 45° C., add pigment dispersion (WSJ24BAMP) slowly under sweep. Use spatula to scrape sides of beaker and ensure thorough mix At 30° C., add preservative under sweep.

Continue the seeping mixing until the mixture reaches room temperature

Procedure to Determine Swelling of a Post-Foaming Gel Composition

The functionality of compositions of the present invention may be evaluated according to the following procedure.

A pair of false eyelashes, preferably made of 100% sterilized human hair (an example is available as ARDELL FASHION LASHES #117) is mounted on the platform of a MORITEX I SCOPE USB video microscope. The scope is mounted on a ring stand so as to immobilize it. It is preferred to use a scope instrument that is equipped with a 30-magnification lens such as the MORITEX I SCOPE USB.

The subject post-foaming composition is then introduced onto the eyelashes with an ordinary mascara brush in the manner mascara compositions are usually applied to eyelashes. Photos are taken before and after the post-foaming gel composition is deposited onto the eyelashes. Furthermore, video can be shot from before the application of the post-foaming composition to a point after the foaming or swelling ceases.

Mascara formulas 2 through 6 were tested in the manner described above. All five examples showed a definite change in surface area. That is it was observed that after application of the post-foaming gel composition to the eyelash, said composition began to foam or swell such that the radius of the composition encasing the lash appeared to steadily increase for about 3 to 4 minutes. Upon completion of this 3 to 4 minute time span, the composition of the current invention remained at this increased radial configuration. This increase in surface area was perceivable with the scope and the human eye as well. Furthermore, even at the increased radial configuration the composition remained pliable on the eyelashes.

Although not wishing to be bound thereby the present inventor theorizes that the present invention may work in the following manner. When the post-foaming cosmetic composition of the present invention is applied to, for example, the eyelashes, the film forming agent component of the gel begins to cure. The gel begins to generate foam causing the film, which is at that point fairly elastic, to expand. The film then sets up and though it is sufficiently rigid to trap the foam contained within it, it remains sufficiently elastic to allow subsequent flex of the eyelash hair fibers upon which the composition is applied, without fracture of the film. The foamed material entrapped by the sufficiently elastic film acts to volumize the eyelashes. When the composition is employed as a mascara the composition will preferably contain an amount of colorant, especially pigment, sufficient to impart color to the hair fibers and more particularly sufficient to mask any coloration of the entrapped foam. When the composition of the present invention is applied to, for example, white hair, inclusion of a color or pigment is unnecessary.

The cosmetic composition of the present invention when applied in the form of a mascara is advantageous in the much fewer brush stokes are required and thus manipulation is greatly reduced. For example, 3 to 5 brush stokes are required rather than the 14 or more brush stokes typically employed with mascara products of the prior art are applied to eyelashes.

Prior art mascara products require a great deal of manipulation to gain the desired effect of volume. Some prior art products are high viscosity or paste like and are usually comprised of waxes, high pigment loads and volatile substances. Such types of mascaras are hard to manipulate and consequently require excess stroking on application to the eyelashes in order to prevent clumping. Other prior art products have a lower viscosity. They use film formers and require multiple applications to build up to a desired level of volume. With all prior art mascara products, the product experiences a loss of volume after application to the eyelashes. This is due to evaporation of solvents which causes the product to actually shrink down. The composition of the present invention eliminates these deficiencies of the prior art. The post-foaming gel of the present invention requires much less manipulation upon application and actually surprisingly increases volume, in a substantially uniform manner, immediately after application to the eyelashes. The properties of the gel of the present invention make it easy to evenly apply same to the eyelashes and thereby eliminating clumping.

The cosmetic composition of the present invention can be used for hair volumizing and consequently it can be used on the hair of the head, eyebrows and eyelashes. As noted earlier, when used for volumizing it can be employed with or without a colorant, such as a pigment. When used on scalp hair that is white, no colorant, is required. However, when used on hair that is other than gray or white, a colorant, such as a pigment, is generally included in the composition of the present invention. Sufficient colorant or pigment should be utilized to mask the color of the entrapped foam, preferably sufficient colorant should be employed to impart to the hair fibers a predetermined desired amount of color. A method of imparting volume to the hair comprises applying the composition of the present invention to the hair, preferably with the aid of an applicator.

Compositions according to the present invention may be packaged in the packaging systems described in U.S. Pat. Nos. 2,995,521; 3,541,581; 3,654,167; 4,405,489; 4,528,111; 4,651,503; 6,165,456 and US Patent Application Publication US 2002/0122772 A1.

It should be understood that the foregoing description is only illustrative of some embodiments of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method for imparting a volumizing effect to eyelashes comprising the step of contacting said eyelashes with a cosmetically acceptable post-foaming gel composition comprising: a film forming agent; a volatile aliphatic hydrocarbon post-foaming component; a surfactant; and a pigment, the volatile aliphatic hydrocarbon post-foaming component causing the surfactant to foam on the eyelashes so that the composition encasing the eyelashes increases in radius.

2. The composition of claim 1, wherein the gel includes about 1 to about 50% by weight of said film-forming agent, based on the total weight of the gel.

3. The composition of claim 1, wherein said film-forming agent is a copolymer.

4. The composition of claim 3, wherein said film-forming agent is selected from the group consisting of an acrylates copolymer, methacrylates copolymer, and mixtures thereof.

5. The composition of claim 1, wherein said pigment is present in an amount sufficient to mask color of foam entrapped by the film-forming agent.

6. The composition of claim 1 wherein said pigment is a pigment dispersion.

7. The composition of claim 6, wherein said pigment dispersion comprises water, an iron oxide and a second film forming agent.

8. The composition of claim 1, wherein the gel further comprises a water-soluble viscosity increasing/gelling agent.

9. The composition of claim 8, wherein said water-soluble viscosity increasing/gelling agent is selected from the group consisting of synthetic sucrose derivatives, cellulose gums and hydrophilic colloids.

10. The composition of claim 1, wherein the gel is water-rinseable.

11. The composition of claim 1, wherein the surfactant is an anionic surfactant.

12. The composition of claim 11, wherein said anionic surfactant is selected from the group consisting of alkyl sulfates, alkyl ether sulfates, alkyl monoglyceryl ether sulfates, alkyl monoglyceride sulfates, alkyl monoglyceride sulfonates, alkyl sulfonates, alkylaryl sulfonates, alkyl sulfosuccinates, alkyl ether sulfosuccinates, alkyl sulfosuccinates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, alkyl ether phosphates, and mixtures thereof.

13. The composition of claim 1, wherein the surfactant is an amphoteric surfactant.

14. The composition of claim 13, wherein the amphoteric surfactant is selected from the group consisting of amphocarboxylates, alkyl betaines, amidoalkyl betaines, amidoalkyl sultaines, amphophosphates, phosphobetaines, pyrophosphobetaines, carboxyalkyl alkyl polyamines, alkyl amino monoacetates, alkyl amino diacetates, and mixtures thereof.

15. The composition of claim 1, wherein the surfactant is a nonionic surfactant.

16. The composition of claim 15, wherein the nonionic surfactant is a polyoxyethylene derivatives of a polyol ester.

17. The composition of claim 1, wherein the film-forming agent is present in an amount sufficient to form a film over greater than about 50% of the surface of the foam or sufficient to increase foam lattice rigidity by greater than about 50%.

18. The composition of claim 1, wherein the film-forming agent is present in an amount sufficient to form a film over greater than about 75% of the surface of the foam or sufficient to increase foam lattice rigidity by greater than about 75%.

19. The composition of claim 1, wherein the film-forming agent is present in an amount sufficient to entrap at least a portion of the foam and, when the film-forming agent sets, maintain the increased radius thereby imparting a volumizing effect to the eyelashes.

20. The composition of claim 19, wherein the composition is pliable at said increased radius.

21. The composition of claim 1, wherein the volatile aliphatic hydrocarbon post-foaming component is selected from the group consisting of n-pentane, isopentane, n-butane, isobutane, isobutene, trichlorofluoroethane, 1,2-dichloro-1, 1,2,2-tetrafluoroethane, neopentane, and mixtures thereof.

22. The composition of claim 1, wherein the volatile aliphatic hydrocarbon post-foaming component has a vapor pressure of from about 6 to about 30 pounds per square inch gauge at a temperature of from about 90° to about 100° F.

* * * * *